United States Patent
Dall et al.

[11] Patent Number: 6,066,141
[45] Date of Patent: May 23, 2000

[54] BONE GRIP

[76] Inventors: Desmond Meiring Dall, 34 Riverside Road, Hermanus 7203, Cape Province, South Africa; Anthony William Miles, 14 Upper Oldfield Park, Bath, BA2 3JZ, United Kingdom

[21] Appl. No.: 09/118,663

[22] Filed: Jul. 17, 1998

[30] Foreign Application Priority Data

Jul. 22, 1997 [GB] United Kingdom ............... 9715440

[51] Int. Cl.[7] .................................................. A61B 17/58
[52] U.S. Cl. ................... 606/74; 606/69; 606/61
[58] Field of Search ............... 606/69, 70, 71, 606/72, 74, 75, 103, 61

[56] References Cited

U.S. PATENT DOCUMENTS

| | | | |
|---|---|---|---|
| 4,201,215 | 5/1980 | Crossett et al. | 128/335 |
| 4,269,180 | 5/1981 | Dall et al. | |
| 5,810,825 | 9/1998 | Huebner | 606/74 |

FOREIGN PATENT DOCUMENTS

| | | |
|---|---|---|
| 0 604 082 A1 | 6/1994 | European Pat. Off. |
| WO 95/03003 A1 | 2/1995 | WIPO |

*Primary Examiner*—Gary Jackson
*Assistant Examiner*—Daphna Shai
*Attorney, Agent, or Firm*—Akin, Gump, Strauss, Hauer & Feld, L.L.P.

[57] ABSTRACT

A bone grip (100; 200; 300) for use with cerclage cables (140, 142, 144) is typically A-shaped, with two side limbs (102, 104; 202, 204; 302, 304) joining to form a rearwardly curving proximal hook (112; 212; 312). There are "horizontal" holes (114, 116; 214, 216; 314, 316) for cerclage cables extending through the side limbs and through a bridge (106; 206; 306). A "vertical" cerclage cable (144) is guided through a tubular end portion of the hook (124; 224; 324). It may be further guided by a groove (130; 230; 330) on the front surface of the grip and/or by passage through a hole (252) in a bridge (250).

11 Claims, 6 Drawing Sheets

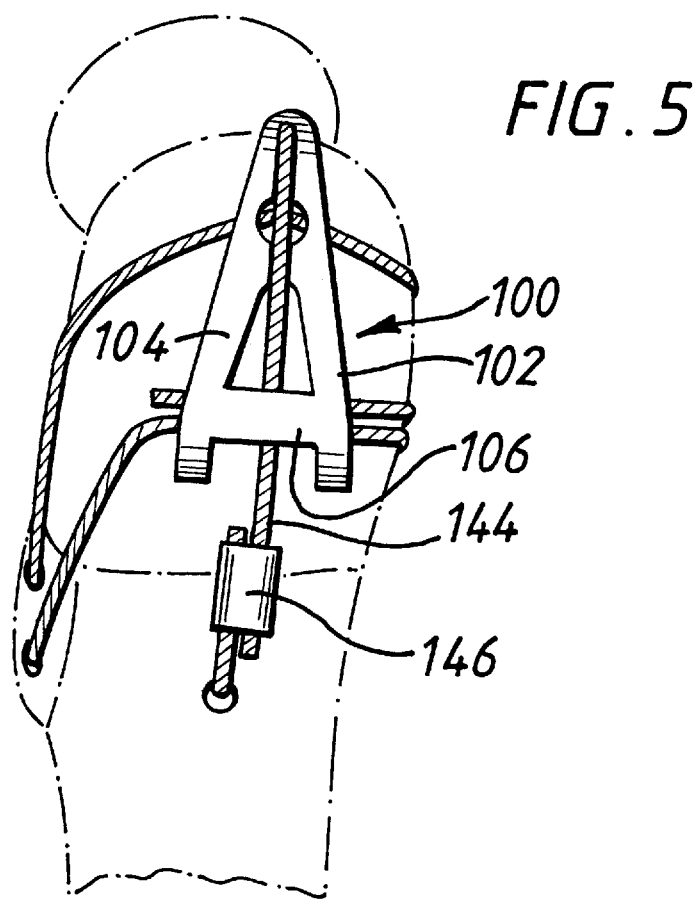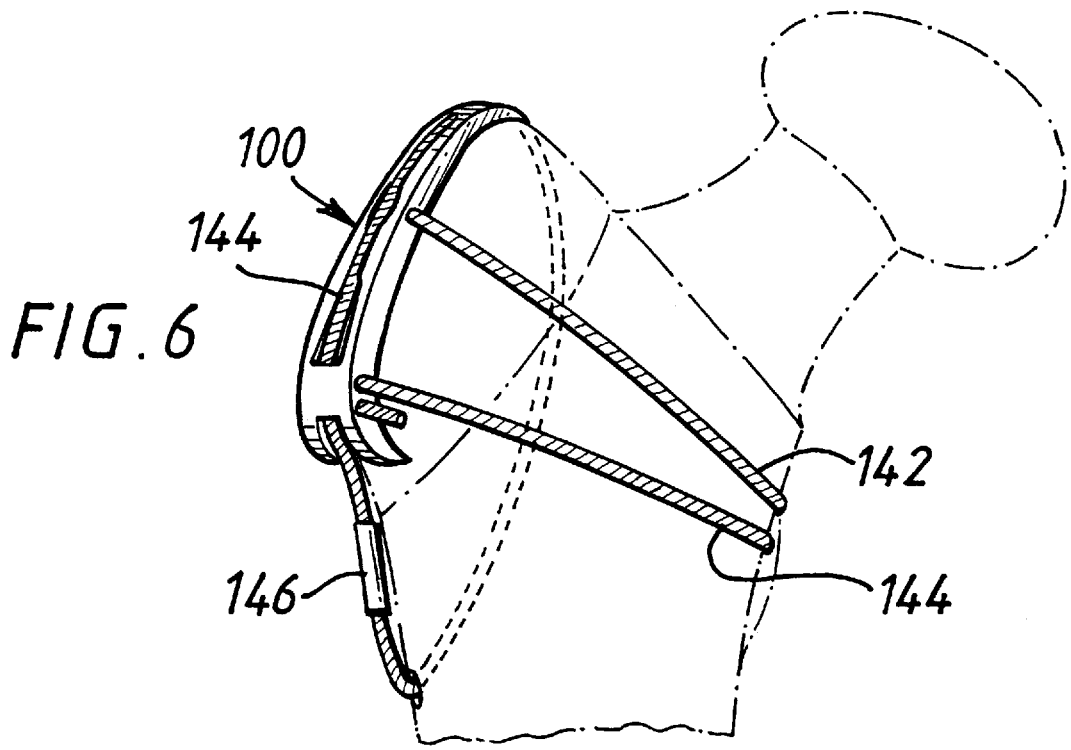

BONE GRIP

BACKGROUND OF THE INVENTION

The present invention relates to a bone grip, and particularly to a bone grip for use in the attachment of the greater trochanter in a total hip replacement operation.

The present inventors have previously developed a range of bone grips for use in hip replacement, and these are described in U.S. Pat. No. 4,269,180. FIG. 1 of the present application is a drawing from that earlier patent, showing a commercially successful embodiment. This is a grip 10 having two parallel side limbs 12 connected by two bridges 14. The limbs curve rearwardly, terminating in upper and lower teeth 16, 18. There are pairs of bores 20 extending completely through the grip, in the regions of the bridges 14.

In a hip replacement operation, part of the greater trochanter may be cut off and has subsequently to be firmly re-attached. For this purpose, it is engaged by a grip 10, which is held in place by cerclage cables which pass through the bores 20 and through holes in the main shaft of the femur. The illustrated grip is for use with two cables. The ends of each cable are passed in opposite directions through the two holes in one of the bridges 14 and tensioned, whereupon the bridge is crimped. The resulting assembly is quite stable, and generally lasts well. However, there are very considerable strains on such a grip, and it is very important that it should hold the trochanter immobile for a period of months. We have found that this design does have a certain tendency to shift in the "vertical" direction (perpendicular to the bridges 14), the motion often approximating to pivoting about one or other of the cables. This is the muscle pull direction, so the forces involved are considerable.

U.S. Pat. No. 4,269,180 discloses also some variants of this design, most of them being generally H-shaped, having a pair of side limbs bridged by a single bridge penetrated by bores. There is also brief mention of a design in the form of a letter A. This is essentially the same as the H-designs, having bores for the cable passing through the bridge (or "cross-bar") of the letter A.

SUMMARY OF THE INVENTION

Broadly, the present invention concerns a bone grip with provisions for at least one "vertical" cable in addition to the conventional "horizontal" cable or cables. Thus there may be formations for guiding and/or retaining a "vertical" cable. These may include one or more of guide groove(s) in the front face of the grip, a guide hole in the proximal end region, and a guide hole in a bridge.

According to the present invention there is provided a bone grip comprising a base structure having a rear face for overlying bone, said base structure comprising a pair of side limbs and at least one bridge extending between the side limbs. At least one hole for a first cerclage cable extends transversely through both side limbs, preferably extending through the at least one bridge (which is then preferably crimpable to lock a cable in the hole). The base structure further provides at least one guide structure to hold and align the second "vertically-acting" cable. For example in one embodiment at one end region the side limbs may curve rearwardly and be shaped to define at least one hook or tooth. At least one hole for a second cerclage cable, running transversely to the first cerclage cable, can be provided through a said hook or tooth e.g. at a proximal end.

Preferably said side limbs coalesce at said one end region. Thus the base structure may be substantially A-shaped. Said coalesced limbs thus curve rearwardly as a single hook or tooth, through which said at least one second cerclage cable extends. There may be a groove on the front face of the base structure for guiding the at least one second cerclage cable towards the hole. There may be a bridge between the side limbs with a transverse hole or holes for guiding and optionally locking the second cable or cables.

Alternatively, or preferably additionally, guide structure for the "vertical" cable can be arranged to hold and align a bight of that cable, e.g. extending away in the distal direction of a femur. This structure may include a bridge extending between the side limbs and defining an arcuate guide path with end holes through the side limbs which incline towards the direction of extension of the second cable, providing cable support without sharp bends.

The grip will be made of surgically acceptable material, e.g. stainless steel, chromium-cobalt or titanium alloy.

Some embodiments of the invention will now be described in more detail with reference to the accompanying drawings.

BRIEF DESCRIPTION OF THE DRAWINGS

FIG. 5 is a perspective view from below of a femur having been subject to a hip replacement operation using the first embodiment of bone grip;

FIG. 6 is a view of the femur of FIG. 5 seen from the right hand below;

DESCRIPTION OF THE PREFERRED EMBODIMENTS

Figure 1:
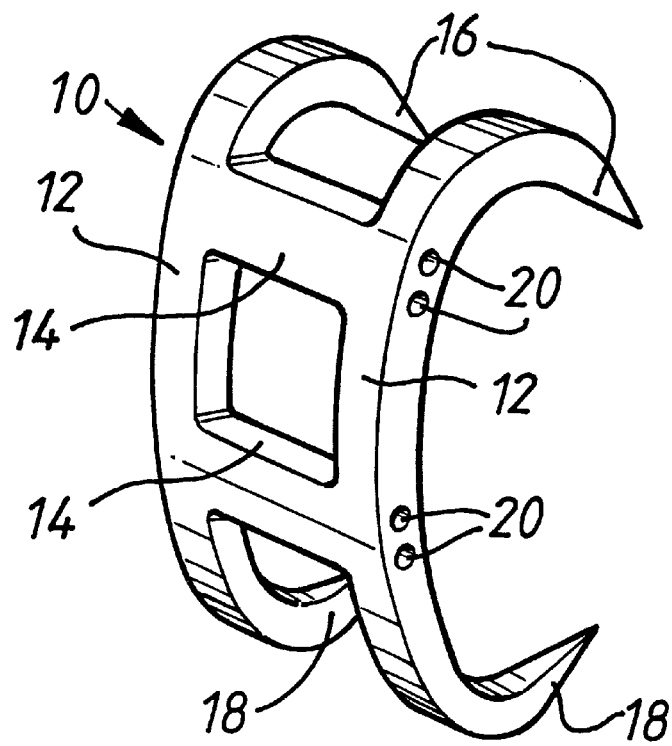
FIG. 1 shows a prior art bone grip.
Figure 2:
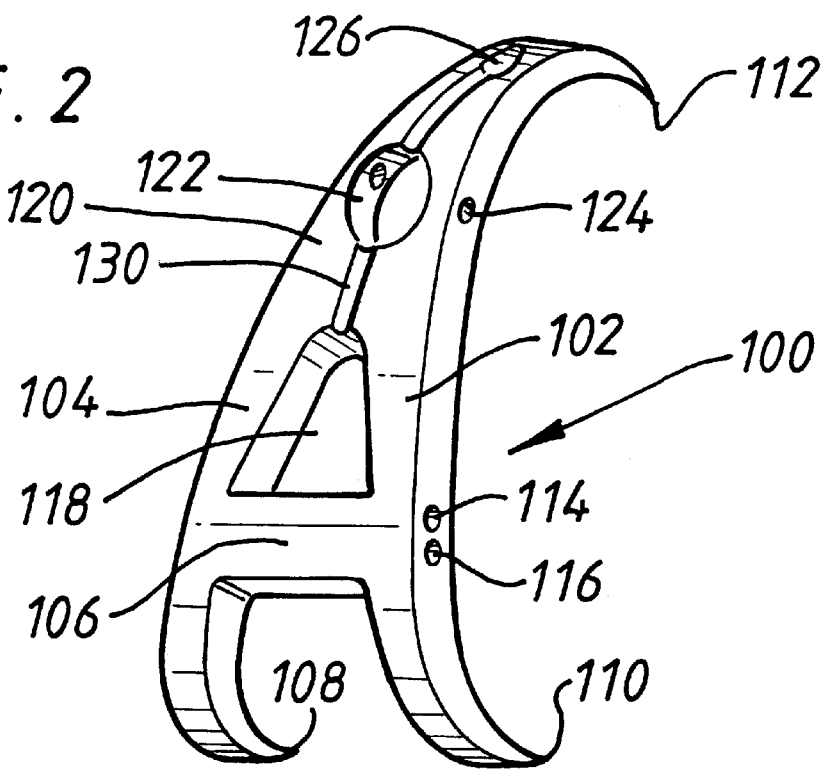
FIG. 2 is a perspective view of a bone grip which is a first embodiment of the invention.
Figure 3:
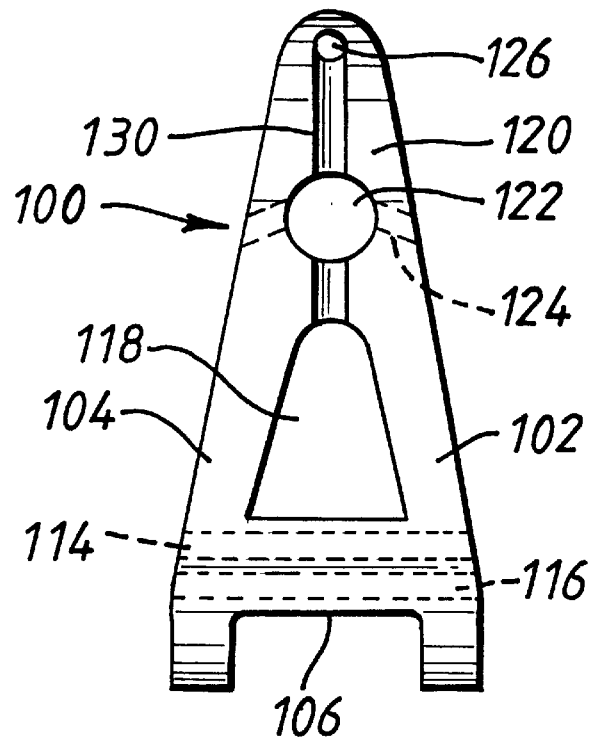
FIG. 3 is a front elevation of the first embodiment.
Figure 4:
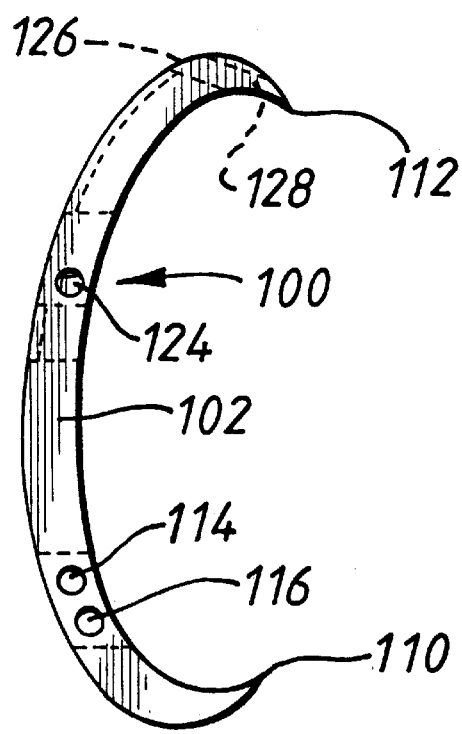
FIG. 4 is a side elevation of the first embodiment.

FIGS. 2 to 4 show a bone grip 100 having a base structure approximating to a letter A, having a pair of side limbs 102, 104 and a single bridge 106. The rear face is curved to conform to the surface of a greater trochanter. Beneath the bridge 106, the side limbs curve rearwardly, ending in distal teeth 108, 110. The top portion also curves rearwardly, forming a proximal hook 112.

A pair of distal bores 114, 116 pass through the side limbs 102, 104 and the bridge 106.

The "A" has a major opening 118 above the bridge 106. Above this opening 118, there is a plate like portion 120 penetrated by a circular opening 122. A proximal cable hole 124 extends through the grip, in the region of the circular hole 122.

The proximal hook 112 is cannulated. That is to say, it is tubular, there being an exit hole 126 for a cable on the top face some way above the circular hole 122, and an entry opening 128 at the end of the hook. A cable groove 130 extends from the exit hole 126 to the circular hole 122 and beyond this, to the opening 118.

Figure 7:
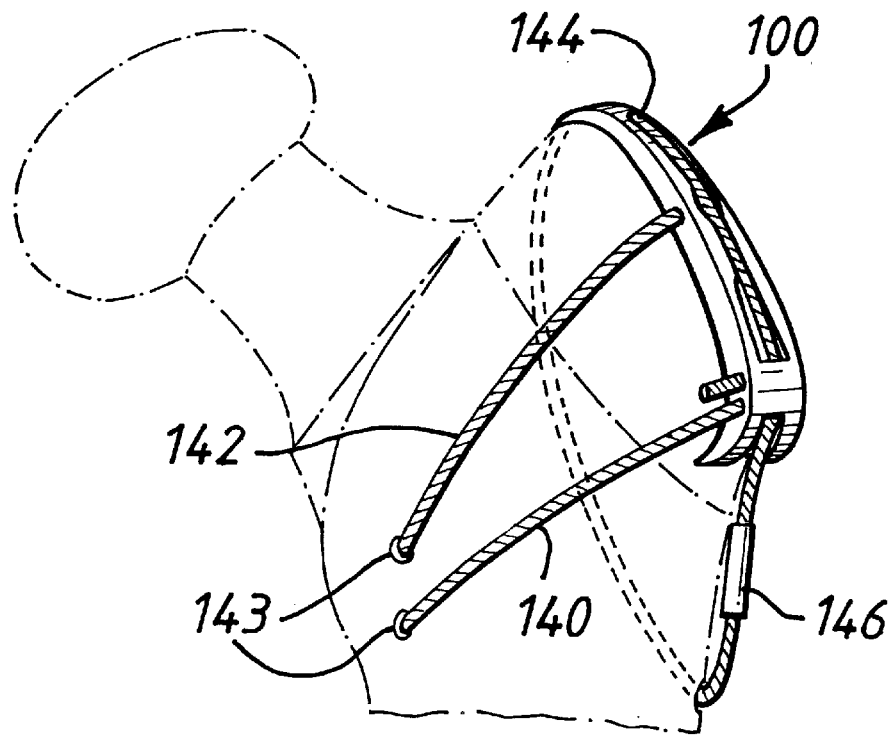
FIG. 7 is a view of the femur of FIG. 5 seen from the left.

As can be seen in FIGS. 5, 6 and 7, the bone grip 100 is mounted to the greater trochanter, and secured to the rest of the femur by cerclage cables 140, 142 which pass through the distal and proximal cable holes 114, 116, 124, in a manner similar to the cerclage cables as used in the prior art discussed above. These cables are shown in FIG. 7 as passing through anchor holes 143 in the lesser trochanter. The distal cable 140 has its two ends passed through respective bores 114,116 which extend through the bridge, which is crimped to lock them in place by means of a crimping tool which grips the edge faces of the bridge (i.e. the face bordering the opening 118 and the oppositely directed face). The proximal cable is engaged in the upper anchor holes 124. It may be a pair of beaded cables, extending out in opposite directions from the circular opening 122.

Additionally, there is a "vertical" cable 144 extending through the vertical cable bore 126. From the entry hole at the tip of the hook 112, this cable passes through the medullary canal, reemerging beneath the bone grip 100. Thus the two ends of the vertical cable 144 can be passed through a conventional crimp sleeve 146, and locked in place.

Figure 8:
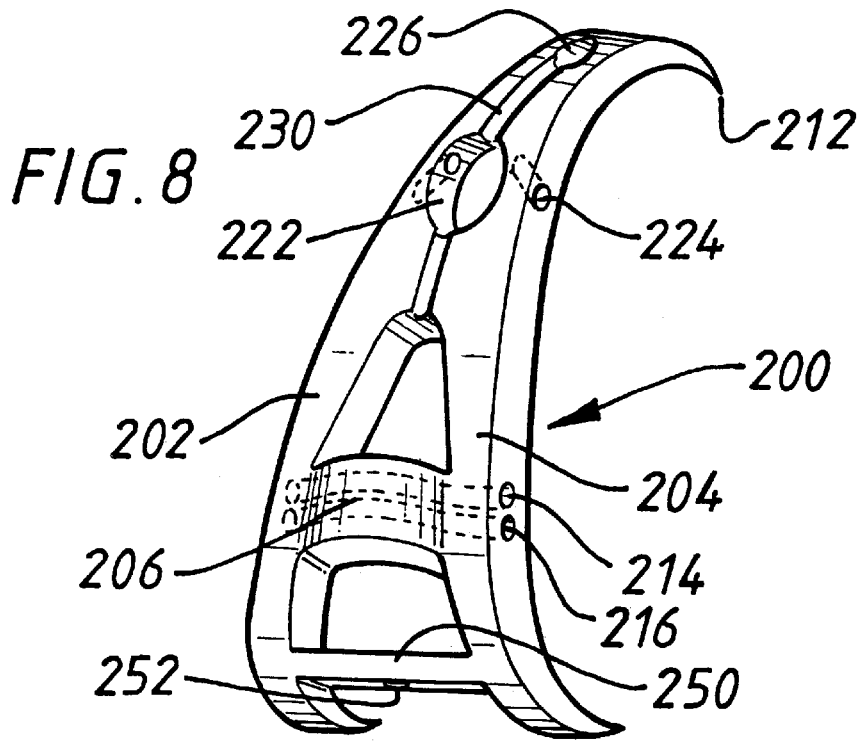
FIG. 8 is a view similar to FIG. 2 but showing a second embodiment of bone grip.

FIG. 8 shows a substantially similar bone grip 200. Elements corresponding to those of the first embodiment have corresponding reference numbers, but raised by 100.

Thus there are side limbs 202, 204, and a distal bridge 206. However in this example, the bridge 206 is curved, projecting forwardly of the adjacent portions of the side limbs, and the bores 214, 216 are correspondingly curved. This facilitates smooth cable passage.

This second embodiment also has a second, minor bridge 250 with a "vertical" bore 252 (extending along the axis of the A), to provide an anchorage for the vertical cable, in this case at the distal end.

Figure 9:
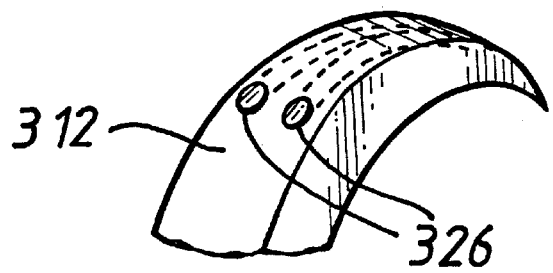
FIG. 9 is a detail of the top hook region of a bone grip showing another possible variant.

FIG. 9 shows a further variation, namely a proximal hook 312 which is doubly cannulated; that is, it has two bores 326 in place of the single bore 126 or 226 shown in FIGS. 2 and 8.

Figure 10:
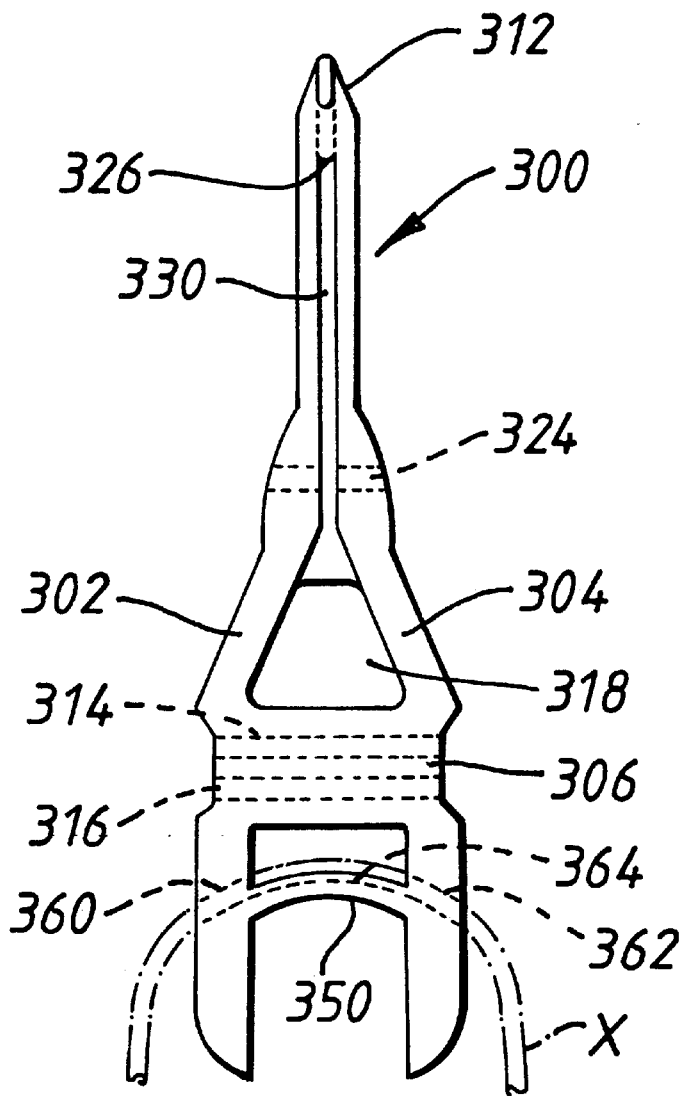
FIG. 10 is a schematic "flattened out" view of a third embodiment.
Figure 11:
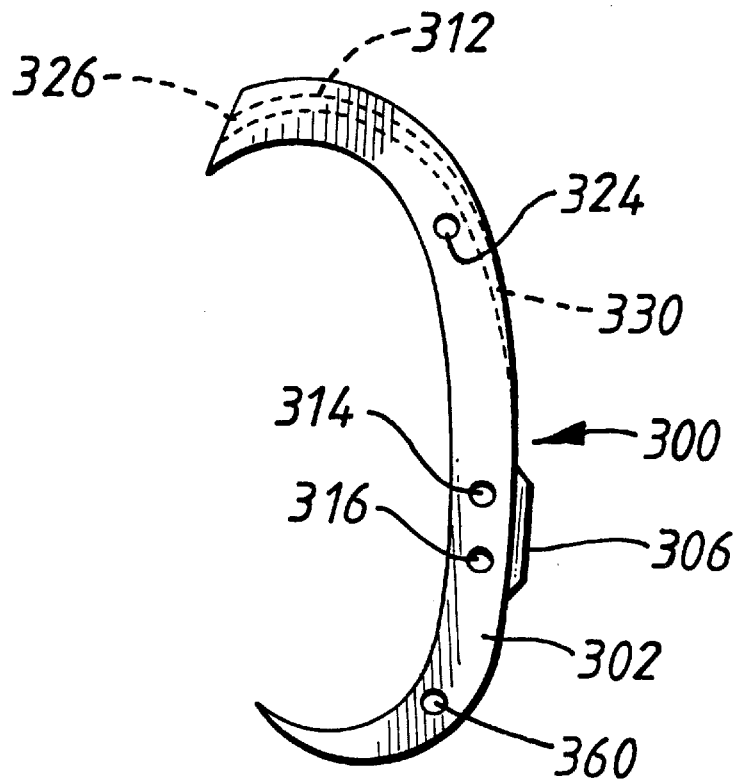
FIG. 11 is a side view of the third embodiment, showing its curvature.

FIGS. 10 and 11 show a bone grip 300 which resembles that shown in FIG. 8 in that it approximates to an A-shape with an additional lower bridge 350. However this lower bridge does not have a "vertical" bore and is curved, being proximally convex. The side limbs 302, 304 have cable openings 360, 362 angled upwardly towards the interior, so as to guide a vertically-acting cable bight to follow the line of the bridge 350, which has a guide formation such as a groove 364 for locating and supporting such a cable bight without kinks: see broken line X in FIG. 10. Alternatively there may be an enclosed bore of proximally-convex path through the lower bridge. The other end of the cable bight can be secured at a relatively distal region of the femur.

As in the second embodiment the main bridge 306 curves out of the plane of FIG. 10, and has two arcuate cable bores 314, 316.

The upper region has a proximal cable hole 324. This may be curved like the lower bores 314,316. However a straight bore 324 permits the grip body to be thinner.

There is no upper central hole as in the previous embodiments (122 in FIG. 2). The cable groove 330 is relatively long, running from adjacent the main opening 318 to the exit hole 326 in the tubular end portion of the proximal hook 312.

Figure 12:
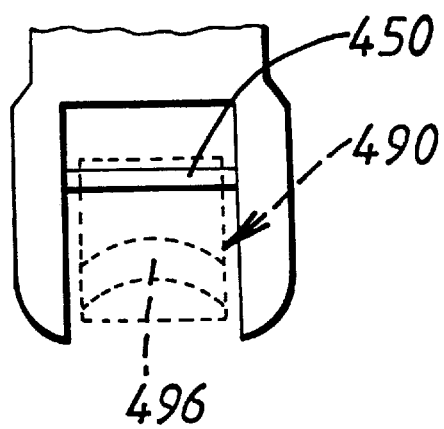
FIG. 12 is a detail of the lower region of a further variant, and also shows a clip-on member.
Figure 13:
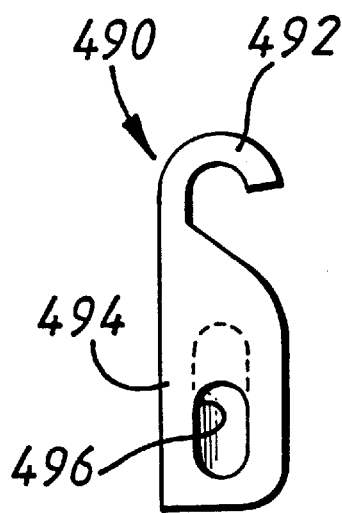
FIG. 13 is a side view of the clip-on member shown in FIG. 12.

FIG. 12 shows an alternative form of distal end region. This has a thin straight bar 450 for the distal (lower) minor bridge. A clip-on member 490 can be hooked onto the bar 450. This member has an upper hook portion 492 (FIG. 13) for the purpose, and a body portion 494 in which a transverse cable bore 496 is defined. As shown in FIG. 12 this may be arcuate (convex upwards). A cable may be passed through this. Its ends may extend downwards and be secured to a distal region of the femur.

The embodiments of FIGS. 10, 11 and 12 offer the user alternative ways of securing a vertically-acting cable. The proximal groove and hole will hold and align a vertically-running cerclage cable passing through the medullary canal, as in FIGS. 5 to 7. Or, the upwardly-convex guide path and hole(s) at the distal bridge will hold and align a vertically acting cable, particularly arranged as a bight, which can be secured at a relatively distal part of the femur by an additional anchorage without needing to pass a cable through the medullary canal.

Whereas the present invention has been described and illustrated with respect to some preferred embodiments, the skilled reader will appreciate that alternatives and modifications are possible. It is intended to include all such alternatives and modifications within the scope of the appended claims.

What is claimed is:

1. A bone grip for use with cerclage cables comprising a base structure having a proximal end region and a distal end region and a rear face for overlying bone, said base structure comprising a pair of side limbs extending from said proximal end region to said distal end region and at least one bridge extending between the side limbs; said side limbs each having at least one transverse hole for receiving a first cerclage cable which bridges said limbs, and said base structure further having at least one longitudinal guide structure extending in the proximal-distal direction to hold and align a second cable acting transversely to the first cerclage cable in the proximal-distal direction.

2. A bone grip according to claim 1 wherein said guide structure is provided by said limbs extending to said proximal end region where they may remain discrete or coalesce to form a common proximal end portion, and where they are shaped to define at least one proximal hole for said second cerclage cable running transversely to the first cerclage cable.

3. A bone grip according to claim 2 wherein said base structure has a front face in which is defined a guide groove for guiding said second cerclage cable towards said proximal hole.

4. A bone grip according to claim 2 including a bridge which extends between said side limbs and in which a transverse hole is provided for guiding said second cerclage cable.

5. A bone grip according to claim 1 wherein said at least one transverse hole extends through said at least one bridge.

6. A bone grip according to claim 5 wherein said bridge is adapted to be crimped to lock a cable in the transverse hole therein.

7. A surgical method comprising gripping bone by means of a bone grip comprising a base structure having a rear face for overlying bone, said base structure comprising a pair of side limbs and at least one bridge extending between the side limbs; said side limbs each having at least one transverse hole for receiving a first cerclage cable which bridges said limbs; said base structure further having at least one guide structure to hold and align a second cable acting transversely to the first; comprising securing the bone grip to bone by means of a first cerclage cable passed through the transverse holes in the side limbs and a second cerclage cable which acts transversely to the first, and is held and aligned by said guide structure.

8. A bone grip for use with cerclage cables comprising a base structure having a rear face for overlying bone, said base structure comprising a pair of side limbs and at least one bridge extending between the side limbs; said side limbs each having at least one transverse hole for receiving a first cerclage cable which bridges said limbs, said base structure further including at least one guide structure to hold and align a second cable acting transversely to the first cerclage cable, the guide structure being defined by said limbs extending to a proximal end region where the limbs may be discrete or coalesce to form a common proximal end portion, and at said proximal end region said limbs of said common proximal end portion curve rearwardly to define at least one hook or tooth which is at least partly tubular to define at least one proximal hole for a second cerclage cable running transversely to the first cerclage cable.

9. A bone grip for use with cerclage cables comprising, a base structure having a rear face for overlying bone, said base structure comprising a pair of side limbs and at least one bridge extending between the side limbs; said side limbs each having at least one transverse hole for receiving a first cerclage cable which bridges said limbs, and said base structure further having at least one guide structure to hold and align a second cable acting transversely to the first cerclage cable, said guide structure for a second cable including a distal bridge extending between the side limbs and defining a proximally-convex guide path for a bight of said second cable, and distally-inclined holes through the side limbs to receive said second cable.

10. A bone grip for use with cerclage cables comprising, a base structure having a rear face for overlying bone, said base structure comprising a pair of side limbs and at least one bridge extending between the side limbs; said side limbs each having at least one transverse hole for receiving a first cerclage cable which bridges said limbs, said base structure further having at least one guide structure to hold and align a second cable acting transversely to the first cerclage cable, said guide structure for a second cable including a clip-on cable guide member having a hook portion for hooking over said bridge and a body portion in which a cable hole is provided.

11. A bone grip for use with cerclage cables comprising, a base structure having a rear face for overlying bone, said base structure comprising a pair of side limbs and at least one bridge extending between the side limbs; said side limbs each having at least one transverse hole for receiving a first cerclage cable which bridges said limbs, said base structure further having at least one guide structure to hold and align a second cable acting transversely to the first cerclage cable, said guide structure for the second cable including a distal bridge extending between the side limbs and end holes through the side limbs which incline towards the direction of extension of the second cable, said distal bridge and said end holes defining an arcuate guide path for the second cable.

\* \* \* \* \*